United States Patent [19]

Pares Farras et al.

[11] Patent Number: 5,114,848
[45] Date of Patent: May 19, 1992

[54] EXTRACELLULAR EXOPOLYMER, PROCESS FOR ITS PREPARATION AND PHARMACEUTICAL COMPOSITIONS CONTAINING THE SAID EXOPOLYMER

[75] Inventors: Ramon Pares Farras, Begues; Juan Jofre Torroella, Tiana, both of Spain; Jean-Paul Ricard, Geneva, Switzerland; Adrian Schulthess, Begnins, Switzerland; Jean-Claude Farine, Eysins, Switzerland; Marie-Christine Michelet, Bouveret, Switzerland; Agnès Ramsteiner, Onex, Switzerland; Jacques Bauer, St-Sulpice, Switzerland

[73] Assignee: Laboratoires OM S.A., Meyrin, Switzerland

[21] Appl. No.: 566,294

[22] Filed: Aug. 9, 1990

[30] Foreign Application Priority Data

Sep. 29, 1989 [CH] Switzerland .................. 3536/89

[51] Int. Cl.$^5$ .................. C12P 19/04; C07H 1/00
[52] U.S. Cl. .................. 435/101; 536/1.1; 536/123
[58] Field of Search .................. 435/101; 536/1.1, 123

[56] References Cited

U.S. PATENT DOCUMENTS

| | | | |
|---|---|---|---|
| 4,435,389 | 3/1984 | Mutai et al. | 536/123 |
| 4,645,667 | 2/1987 | Hashimoto et al. | 424/92 |
| 4,797,589 | 1/1989 | Nakaya et al. | 536/1.1 |

FOREIGN PATENT DOCUMENTS 0201332 11/1986 European Pat. Off. .
0295961 12/1988 European Pat. Off. .
58-203913 11/1983 Japan .

OTHER PUBLICATIONS

Shimamura et al., *Agric. Biol. Chem.*, vol. 54 (11), p. 2869, 1990.
"Structural Studies of Cell Wall Polysaccharides from *Bifidobacterium breve* YIT 4010 and Related Bifidobacterium Species", *Journal of Biochemistry*, vol. 102, No. 6, 1987, by Y. Habu et al., pp. 1423–1432.

Primary Examiner—Johnnie R. Brown
Assistant Examiner—Pamela S. Webber
Attorney, Agent, or Firm—Young & Thompson

[57] ABSTRACT

An extracellular exopolymer endowed with immunomodulating properties is prepared by culturing the *Bifidobacterium infantis longum* strain deposited at the Institut Pasteur under No. I-885 in a suitable medium under anaerobic conditions. After the microorganisms are discarded from the culture medium, the exopolymer thus produced is isolated, concentrated and then precipitated by adding an organic solvent; finally the product resulting from the precipitation is lyophilized.

The exopolymer thus obtained possesses an activity on cellular as well as on humoral immunity, and could thus be used as an immunomodulating agent in any potential therapeutic application.

5 Claims, No Drawings

EXTRACELLULAR EXOPOLYMER, PROCESS FOR ITS PREPARATION AND PHARMACEUTICAL COMPOSITIONS CONTAINING THE SAID EXOPOLYMER

The present invention refers to an extracellular exopolymer produced by culturing selected bacterial strains of the genus Bifidobacterium and endowed with immunomodulatory properties. The present invention also covers a process for preparing this exopolymer as well as to pharmaceuticals containing the said exopolymer as active principle.

Numerous ailments such as allergies, autoimmune diseases, certain infectious diseases and certain cancers have as their common denominator a primary or secondary disorder of the immune system. While primary immunodeficiencies are rare and generally have genetic causes, secondary immunodeficiencies are more frequent, and their causes are mostly extrinsic and include for instance recurrent infections, aging, cancer, malnutrition, exposure to immunotoxic substances and stress.

Immunotherapy allows to palliate symptoms of primary immunodeficiencies and to restore the immune status in the event of secondary immunodeficiencies.

Many immunotherapeutic agents have been developed in the form of either immunostimulants or immunosuppressants. Generally, immunomodulators are agents that nonspecifically improve the host's specific reactivity and nonspecific effector mechanisms. A distinction can be made between synthetic immunomodulators and immunomodulators of biological origin. The latter are microbial products and extracts of animal or of even human origin such as for example thymic hormones, dialyzable extracts of leukocytes, interferons and cytokines.

In fact, the activation of lymphocytes or macrophages and their intermodulations are significantly modified by exposure to structural molecules of microorganisms or to biologically active components produced by microorganisms. A wide variety of bacteria and bacterial products have demonstrated their influence on the immune system. This arsenal of immunomodulatory agents of bacterial origin includes mycobacteria and their products, lipopolysaccharides of gram− bacteria, enterotoxins of *Vibrio cholerae*, products of Streptococcus, lipoproteins and glycoproteins of various gram− bacteria, and polysaccharides of various origins. Intensive research is currently under way in this field.

The present invention adds another element to the field of immunotherapy, since it refers to a new extracellular exopolymer endowed with highly interesting immunomodulatory properties. More precisely, the present invention covers the said exopolymer produced by the described process as defined in claim 1 as well as the process for obtaining the extracellular exopolymer. Other items of the present invention will be developed hereafter.

The exopolymer, which is the subject of the present invention, has been produced by culturing selected strains of a newly isolated species *Bifidobacterium infantis longum*, a gram+ bacterium, which is presenting taxonomic characteristics between *Bifidobacterium infantis* and *Bifidobacterium longum*. Possessing immunomodulatory properties demonstrated experimentally, this exopolymer is thus of real interest to human and veterinary medicine.

The process covered by the present invention is characterized by the fact that the bacterial strain 1BS of *Bifidobacterium infantis longum* deposited under No I-885 at the Institut Pasteur—Collection Nationale de Culture de Microorganismes (CNCM)—is cultured under anaerobic conditions in a suitable medium and that after discarding the microorganisms from the culture medium the exopolymer thus produced is isolated, concentrated and then precipitated by adding an organic solvent. Finally, the product resulting from the precipitation is lyophilized.

The strain 1BS can be cultured in any type of suitable medium whose components have a molecular weight inferior to 10,000 daltons, under anaerobic conditions, preferably at about 37° C. The detailed composition of such a medium is described below.

Upon culturing, the colonies are white and mucous of more than one millimeter diameter after 48 hours anaerobic incubation at 37° C. in RCA medium. The bacteria are Gram positive, pleomorphic, and catalase negative.

The microorganisms are discarded from the culture medium preferably by centrifugation, the exopolymer is isolated, for instance by ultrafiltration on a calibrated porous membrane with a retention threshold higher than, or equal to, 10,000 daltons.

The product thus isolated is then concentrated, dialyzed, precipitated by adding an organic solvent, preferably ethanol, and finally lyophilized.

The resulting exopolymer is essentially of polysaccharidic nature, composed primarily of glucose and galactose in the ratio from 1:1 to 4:1 and contains a proteinic fraction at most equal to 30% in weight. Within the polysaccharide fraction, the proportion of glucose and galactose is in the range from 1:1 to 4:1, preferably about 3:2.

The exopolymer of the present invention has an apparent molecular weight of 10,000 to 100,000 daltons, preferably 20,000 to 30,000 daltons. It can form aggregates of a molecular weight of about $10^6$ daltons in equilibrium with the units of lower molecular weight. It is also free of nucleic acids, lipids and organic acids.

The exopolymer thus isolated and purified has interesting immunomodulatory properties while being nontoxic. Both in-vitro and in-vivo experiments have shown that the exopolymer produced from the strain 1BS behaves like an immunomodulator and that it enhances the host's nonspecific resistance. It also has definite antileukemic (antitumoral) properties whose origin may be linked to its immunomodulator properties described in "Determination of the immunomodulator properties of the exopolymer produced by the strain 1BS".

Thus, the exopolymer produced by the strain 1BS can be advantageously used as the active principle of various pharmaceuticals that can be administered orally, parenterally as well as locally. These pharmaceuticals can be presented in forms commonly used in human or veterinary medicine, e.g., in the form of simple or sugar-coated tablets, capsules, small pills, solutions, syrups, suppositories, injectable preparations, pessaries, creams, pomades, lotions, drops and eye lotions. They are all prepared by the usual methods.

The active principle (exopolymer) can be incorporated into such pharmaceuticals alone or together with other pharmacologically active agents. The excipients used for this purpose are common excipients such as talc, arabic gum, mannitol, starch, magnesium stearate, cocoa butter, aqueous or nonaqueous vehicles, greasy substances of animal or plant origin, paraffin derivatives, glycols, various wetting, dispersing or emulsifying agents and preservatives.

In animal significant immunomodulatory effects on mice have been observed for doses between 4-400 µg per mouse.

The examples presented hereafter intend to illustrate the present invention without limiting it. They concern more particularly the preparation of the exopolymer (also named PB3D) and its pharmacological actions.

PREPARATION OF THE EXOPOLYMER BY CULTURE OF THE BACTERIAL STRAIN 1BS OF BIFIDOBACTERIUM INFANTIS LONGUM

Stage A: culture of the strain 1BS

The strain 1BS is cultured under anaerobic conditions at 37° C. (the air being eliminated at the beginning of fermentation) in the following nutrient medium:

| | |
|---|---|
| Peptone (MW < 10'000 daltons) | 5 g/l |
| NaCl | 3 g/l |
| Glucose | 10 g/l |
| Cysteine | 0.5 g/l |
| Sodium acetate | 2 g/l |
| $Na_2HPO_4$ | 2.87 g/l |
| $KH_2PO_4$ | 1.12 g/l |
| $MgSO_4$ | 0.09 g/l |
| $NaH_2PO_4$ | 0.15 g/l |
| $NaHCO_3$ | 2.2 g/l |
| Tween | 1 ml/l |
| Vitamin solution | 10 ml/l |

A solid support such as CYTODEX ® or equivalent can be advantageously added to the culture medium to improve the yield. In these conditions, the strain 1BS produces an exopolymer that can be quantified in the supernatant using an ELISA test method developed for this purpose and described later.

Example 10 liters of the above-defined culture medium are prepared and placed in a 12-liter fermentor for sterilization. The fermentor is then inoculated with 1000 ml of a culture of the 1BS strain cultured in the same medium for 48 hours. A mixture of 90% $N_2$ and 10% $CO_2$ is bubbled for 20 minutes at the rate of 3 liters per minute.

Incubation is performed at 37° C. with stirring at 400 rpm under an $N_2/CO_2$ mixture in the usual ratio which is injected into the medium during the first two hours of fermentation. After 48 hours, upon completion of the fermentation process, the amount of polysaccharide produced is determined by the ELISA method. The minimum yield is 35 µg/ml.

Stage B: isolation and purification of the exopolymer produced

Upon completion of the fermentation process, the cells are separated by centrifugation. Once the cells sedimented the supernatant is ultrafiltered using an apparatus of the type Amicon Hallow Fiber H5 P10-43. Only the molecules heavier than 10,000 daltons are retained. The solution containing the exopolymer produced is concentrated tenfold and then dialyzed.

The concentrated solution is precipitated with alcohol (ethanol:water; 3:1 v/v).

Finally, the product precipitated with ethanol is lyophilized. The product thus obtained is whitish and looks fibrous.

Example

From the above culture, 10 liters of supernatant liquid are obtained and then concentrated to 1 liter by ultrafiltration. The volume is adjusted to 10 liters with distilled water and then reduced again by ultrafiltration to about 1 liter. This operation is performed twice. The 1-liter concentrated solution thus obtained is then precipitated with ethanol (3:1, v/v). The resulting precipitate is lyophilized to produce about 400 mg of lyophilizate.

THE ELISA method

The antigen used is a polysaccharide preparation whose purity is ensured by additional deproteinization with phenol. An initial dose of 0.5 mg is injected to a rabbit in two injections—one intraperitoneal and the other subcutaneous—together with complete Freund's adjuvant.

The injection is repeated on the 15th day using this time incomplete Freund's adjuvant. Fifteen days later, the rabbit is bled to obtain an antiserum with high antibody levels that make it possible, by the ELISA method, to recognize the exopolymer purified by chromatography on a SEPHADEX G 200 column and the exopolymer present in the supernatant of the cultures of Bifidobacterium after precipitation with ethanol.

The ELISA test is performed in a microplate. The antigen is adsorbed. Then sites left vacant are filled with serum albumin in the wells. An incubation is then performed with the specific antibodies obtained from the rabbit. Then the antibodies directed against the rabbit's antibodies are added. They are conjugated to alkaline phosphatase. Finally, the substrate (orthonitrophenylphosphate) is added. After incubation the reaction is stopped using NaOH 3M. Optical density (absorbance) is measured at 405 nm on an ELISA reader. By this procedure sufficiently high antibody titres are obtained to permit positive reading for $10^{-4}$ dilutions of antiserum for purified antigens concentrations of 4 µg.

Characterization of the exopolymer produced by the strain 1BS

1) The product obtained consists essentially of glucides (measured by the phenol/sulfuric acid method) and proteins (measured by the Lowry method) in the ratio 5:1.

The product does not contain any nucleic acids according to the analytical results obtained by ion-exclusion chromatography or by gas chromatography. In no case does the hydrolyzate contain any pentoses. The product is free of lipids according to the results obtained by gas chromatography after extraction with n-heptane. There are no organic acids according to the measurements made by ion-exclusion chromatography.

2) According to the results obtained by high-performance liquid chromatography (HPLC) on an RP-8 300 Å column, the product is of glycoproteinic nature.

3) The glucide part is composed of glucose and galactose according to the analysical proofs obtained by ion-exclusion, thin-layer and gas chromatography.

4) Glucose and galactose are present in the ratio 3:2 according to the results obtained by gas chromatography from the monomers hydrolyzed by methanolysis and then acetylated by trifluoroacetylation.

5) The polysaccharide part is ramified with the linkages 1-2, 1-3, 1-4, and 1-6 according to the chromatogram obtained by gas chromatography from the methylated (by methanolysis) and then acetylated monomers (by trifluoroacetylation).

6) The biological activity, which is measured by the ability to stimulate an increase in the number of plaque-forming cells (PFC), originates from the glucidic part and is maintained after treatment with proteinase K damaging the proteinic part.

7) The approximate molecular weight varies between 20'000 and 30'000 daltons according to the results obtained by chromatography on a SEPHADEX G 200 (peak of low molecular weight).

The exopolymer can form aggregates of molecular weight of about $10^6$ daltons in equilibrium with the units of lower molecular weight.

DETERMINATION OF THE IMMUNOMODULATORY PROPERTIES OF THE EXOPOLYMER PRODUCED BY THE STRAIN 1BS (IN VITRO PROOF)

Proliferation of splenocytes

The proliferation of splenocytes in the presence of mitogens can be measured by the reduction of MIT (3-(4,5-dimethylthiazol-2yl)-2,5-diphenyl tetrazolium bromide) to formazan by the mitochondrial dehydrogenase.

Example

The proliferation (splenocytes of mouse C57BL/6) is expressed by optical density (absorbance) at 560 nm as a function of the concentration of PB3D or of the LPS serving as a reference:

| PB3D | | LPS | |
|---|---|---|---|
| μg/ml | OD at 560 nm | μg/ml | OD at 560 nm |
| 333 | 1.483 | 20 | 1.486 |
| 111 | 1.593 | 6.77 | 1.308 |
| 37 | 1.459 | 2.22 | 0.964 |
| 12.3 | 1.018 | 0.74 | 0.725 |
| 4.1 | 0.580 | 0.25 | 0.526 |
| 1.4 | 0.427 | 0.08 | 0.423 |
| Control 0 | 0.273 | 0.03 | 0.366 |
| | | Control 0 | 0.273 |

The PB3D induces a proliferation that is slightly lower than that induced by the LPS.

DETERMINATION OF THE IMMUNOMODULATORY PROPERTIES OF THE EXOPOLYMER PRODUCED BY THE STRAIN 1BS (IN VIVO PROOFS)

Stimulation of the production of antibody-synthesis cells

In the mouse, the exopolymer nonspecifically stimulates the production of antibody-synthesizing cells when administered orally together with sheep's red blood cells or intraperitoneally without sheep's red blood cells. The exopolymer also normalized this capacity in the mouse immunosuppressed with cyclophosphamide.

Example

After a five-day oral administration of PB3D and a booster dose on the 19th and 20th days (organigram A) or without a booster dose (organigram B), an increase in the number of PFCs is observed in the mouse's spleen, depending on the doses administered.

| | | SRBC | PFC/$10^6$ cells | PFC/spleen |
|---|---|---|---|---|
| Organigram A: (with booster) | 400 μg | 100% | 126%* | 136%* |
| | | 100% | 134%* | 145%* |
| | | 100% | 131%* | 143%* |
| | 40 μg | 100% | 115%* | 123%* |
| | | 100% | 125%* | 133%* |
| | | 100% | 120%* | 128%* |
| Organigram B: | 400 μg | 100% | 104% | 104% |
| | | 100% | 109%* | 104% |
| | | 100% | 101% | 101% |
| | 40 μg | 100% | 111%* | 113%* |
| | | 100% | 117%* | 123%* |
| | | 100% | 110%* | 113%* |

* = $p < 0.05$

Example

After intraperitoneal administration of a single dose of 400 μg/mouse of PB3D, a significant increase in the number of PFCs is observed after four days.

| Inoculated product | PFC/spleen | Test group/control group ratio |
|---|---|---|
| Control | 12.5 ± 0 | |
| PB3D | 43.75 ± 31.37 | 3.5 |
| Control | 6.25 ± 6.85 | |
| PB3D | 27.08 ± 24.26 | 4.3 |

Example

The exopolymer administered to mice immunosuppressed with cyclophosphamide makes it possible to observe in the treated mice lower immunosuppression or faster restoration of the normal number of PFCs by comparison with the untreated mice.

| Days after immuno-suppression | Treatment | PFC/spleen | PFC/$10^8$ lymphocytes |
|---|---|---|---|
| 5 | CY[1] | 1.04 ± 2.25 | 30 ± 73 |
| | PB[2] | 4.71 ± 7.32 | 83 ± 146 |
| 7 | CY | 0 | |
| | PB | 7.29 ± 6.14 | 81 ± 84 |
| 10 | CY | 18.75 ± 13.11 | 46 ± 38 |
| | PB | 60.41 ± 64.4 | 382 ± 508 |
| 19 | CY | 25 ± 10.2 | 110 ± 96 |
| | PB | 18.75 ± 8.83 | 86 ± 83 |
| | Controls[3] | 9.5 ± 8.75 | 58.31 ± 49.2 |

[1] Mice immunosuppressed with cyclophosphamide.
[2] Mice immunosuppressed with cyclophosphamide and given PB3D later.
[3] Mice given a saline solution.

Influence on the composition of serum proteins

Various immunomodulators modify the immunoelectrophoretic pattern of the serum proteins recognized as X, LA and LB. The exopolymer covered by the present invention causes such a modification.

Example

The intraperitoneal administration of 400 μg/mouse of PB3D causes after 24 hours and after four days a modification in the serum proteins comparable to that caused by the lipopolysaccharide of Escherichia coli (LPS).

Example

Likewise, the total administration of 400 μg by oral route and splitted into 5 consecutive daily dosis of 80 μg causes a modification in the proteins perceptible five days after administration of the exopolymer.

Colloidal carbon clearance

The exopolymer is administered intravenously (2.5 mg/mouse) to Balb/c mice. After 48 hours, 0.2 ml of a suspension of colloidal carbon is injected intravenously. The disappearance of carbon in the blood, called clearance, is expressed by the logarithmic slope of the carbon level versus time. The exopolymer enhances the clearance.

| Time (min) | Control $H_2O$—NaCl 0.9% | Treated PB3D 2.5 mg |
|---|---|---|
| 0 | 1.865 ± 0.087 | 1.815 ± 0.044 |
| 2 | 1.800 ± 0.031 | 1.662 ± 0.037 |
| 4 | 1.754 ± 0.032 | 1.531 ± 0.065 |
| 6 | 1.588 ± 0.009 | 1.432 ± 0.096 |
| 8 | 1.657 ± 0.038 | 1.305 ± 0.073 |
| 10 | 1.535 ± 0.134 | 1.207 ± 0.105 |
| 12 | 1.588 ± 0.045 | 1.079 ± 0.154 |

Increase of the nonspecific resistance

In the mice immunosuppressed with cyclophosphamide and exposed to cold, it was possible to observe that the exopolymer covered by the present invention increases the hosts' nonspecific resistance to a bacterial infection such as the one provoked by Pseudomonas at the level of mucous membranes or to a viral infection (Coxsackie B virus).

Example

Immunosuppression is conferred by intraperitoneal administration of 200 mg/kg of cyclophosphamide. On the third day, the five-day oral treatment with the exopolymer (80 μg/mouse/day) begins.

The control mice receive an equivalent amount of saline. A few hours after the end of treatment, the mice are infected intranasally with a strain of *Pseudomonas aeruginosa* made pathogenic for the mouse. The survival rate is higher for the treated mice group:

| Experiment | Treatment | Survival (%) rate |
|---|---|---|
| 1 | Control | 8/18 (44) |
|   | 400 μg PB3D | 11/20 (55) |
| 2 | Control | 0/14 (0) |
|   | 400 μg PB3D | 10/29 (34) |
| 3 | Control | 7/12 (58) |
|   | 400 μg PB3D | 9/12 (82) |

Example

Immunosuppression is conferred by a single introperitoneal administration of 200 mg/kg of cyclophosphamide. On the third day, the five-day oral treatment with the exopolymer (80 μg/mouse/day) begins. The control mice receive an equivalent amount of saline. A few hours after the end of treatment, the mice are infected intraperitoneally with Coxsackie B5 virus (0.5 ml with $10^7$ PFU) and the survival rate evaluated. It is higher for the treated mice group:

| Treatment | Conditions after infection | Survival (%) rate |
|---|---|---|
| Control | 4–6° C. | 0/20 (0) |
| PB3D | 4–6° C. | 16/20 (80) |
| Control | 20° C. | 6/10 (60) |
| PB3D | 20° C. | 10/10 (100) |

Tests of spontaneous or induced leukemia

The exopolymer covered by the present invention is capable of delaying the appearance of leukemia in the AKR mice (strain of inbred mice developing spontaneous leukemia very frequently). The exopolymer is also able to delay in the RF mice the appearance of leukemia induced by a carcinogenic substance such as methylcholanthrene. (The strain RF is an inbred strain in which methylcholanthrene causes spontaneous leukemia to appear rapidly).

Example

Two groups of AKR mice were orally given a five-day PB3D therapy every month, while a third group did not receive the test product and served as a control group. Of the two treated groups, one was given a total monthly dose of 400 μg (80 μg/mouse/day for five consecutive days), while the other received a total monthly dose of 4 μg (0,8 μg/mouse/day for five consecutive days).

The results obtained showed a delay in the appearance of leukemia in the treated mice. This difference was clearly significant in the group receiving a total monthly dose of 400 μg. It was confirmed by another experiment during which the treated groups received 400 μg and 40 μg of PB3D respectively.

| | Experiment 1 | | |
|---|---|---|---|
| | Lymphoma incidence (%) | | |
| Age (days) | PB3D 400 μg | PB3D 4 μg | Controls |
| 210 | 5 | 0 | 19 |
| 225 | 5 | 0 | 26 |
| 240 | 11 | 10 | 40 |
| 255 | 21 | 10 | 48 |
| 270 | 26 | 44 | 55 |
| 285 | 37 | 55 | 62 |
| 300 | 37 | 55 | 65 |
| 315 | 42 | 61 | 79 |
| 330 | 47 | 67 | 83 |
| 345 | 55 | 72 | 91 |
| 360 | 61 | 78 | 93 |
| 375 | 65 | 78 | 98 |
| 390 | 71 | 83 | 100 |
| 405 | 71 | 83 | 100 |
| 420 | 76 | 83 | 100 |
| 435 | 76 | 83 | 100 |
| 450 | 76 | 83 | 100 |
| 465 | 76 | 89 | 100 |
| 480 | 76 | 89 | 100 |
| 495 | 82 | 94 | 100 |

| | Experiment 2 | | |
|---|---|---|---|
| | Lymphoma incidence (%) | | |
| Age (days) | PB3D 400 μg | PB3D 40 μg | Controls |
| 168 | 0 | 5 | 5 |
| 175 | 0 | 10 | 5 |
| 182 | 5 | 10 | 5 |
| 196 | 5 | 15 | 5 |
| 203 | 5 | 15 | 11 |
| 210 | 10 | 20 | 11 |
| 217 | 15 | 30 | 11 |

Experiment 2

| Age (days) | Lymphoma incidence (%) | | |
|---|---|---|---|
| | PB3D 400 μg | PB3D 40 μg | Controls |
| 224 | 15 | 30 | 16 |
| 231 | 20 | 30 | 26 |
| 238 | 25 | 30 | 26 |
| 245 | 25 | 30 | 32 |
| 252 | 25 | 40 | 32 |
| 259 | 30 | 40 | 42 |
| 273 | 37 | 45 | 47 |
| 280 | 42 | 45 | 53 |
| 287 | 53 | 50 | 53 |
| 294 | 53 | 55 | 58 |
| 301 | 53 | 60 | 58 |
| 308 | 53 | 65 | 58 |
| 315 | 53 | 65 | 63 |
| 336 | 60 | 65 | 63 |
| 343 | 60 | 65 | 68 |
| 350 | 60 | 70 | 68 |
| 406 | 65 | 70 | 74 |
| 462 | 65 | 80 | 84 |
| 518 | 80 | 85 | 95 |
| 560 | 80 | 85 | 100 |

Example

During the two months preceeding the topical administration of methylcholanthrene, two groups of RF mice received two oral administrations of PB3 D three weeks apart. One of the groups was given a monthly total dose of 400 μg (80 μg/day/mouse for five consecutive days), while the other received a monthly total dose of 4 μg (0.8 μg/day/mouse for five consecutive days). The control group received no treatment. Leukemia was induced by cutaneous application on a properly shaved area of the body. The administration of PB3D delayed the appearance of leukemia. This delay was clearly significant in the group receiving 400 μg of PB3D.

| Time after treatment with methylcholanthrene (days) | Age (days) | Lymphoma incidence (%) | | |
|---|---|---|---|---|
| | | PB3D 400 μg | PB3D 4 μg | Controls |
| 50 | 170 | 0 | 6 | 14 |
| 80 | 200 | 10 | 25 | 60 |
| 110 | 230 | 25 | 44 | 75 |
| 140 | 260 | 35 | 62 | 83 |
| 170 | 290 | 55 | 69 | 95 |
| 190 | 310 | 55 | 69 | 100 |
| 220 | 340 | 55 | 81 | 100 |
| 250 | 370 | 55 | 100 | 100 |
| 280 | 400 | 60 | 100 | 100 |
| 290 | 410 | 65 | 100 | 100 |

Acute toxicity

Acute toxicity tests have been conducted by intraveneous injection of the exopolymer at the following doses: 1 μg, 10 μg, 15 μg, 100 μg, 300 μg, 600 μg and 1200 μg per mouse into the caudal vein of five mice for each dose. No dose produced any negative reactions in the mice that were still alive two months after the injection.

Description of the strain

The strain 1BS of *Bifidobacterium infantis longum* was deposited on Jul. 6th, 1989 at the "Collection Nationale de Cultures de Microorganismes" (Institut Pasteur, 25 rue du Docteur Roux, 75724 Paris, Cedex, France). It bears the deposit number I-885.

This strain was isolated from wastewater containing fecal matter of human origin and presents taxonomic characteristics between *Bifidobacterium infantis* and *Bifidobacterium longum* and is typable by the profile of the structural components, the profiles of the fermentation catabolites of D-glucose, the profile of resistance to antibiotics and the production of the exopolymer covered by the present invention.

We claim:

1. A method of producing an extracellular exopolymer, comprising culturing a biologically pure culture of Sp. *Bifidobacterium infantis longum* having all the identifying characteristics of CNCM No. I-885 in a culture medium, separating the microorganisms from the cultured medium, and separating from the cultured medium an exopolymer having an apparent molecular weight of 10,000-100,000 daltons, free of nucleic acids and lipids and organic acids, which is polysaccharidic in nature and comprises primarily glucose and galactose in the ration between 1:1 and 4:1.

2. A method as claimed in claim 1, wherein the ratio of glucose to galactose is about 3:2.

3. A method as claimed in claim 1, in which said apparent molecular weight is from 20,000-30,000 daltons.

4. An exopolymer produced by the method of claim 1.

5. A method as claimed in claim 1, in which said extracellular exopolymer has immunomodulatory, antiinfective and antitumoral properties.

* * * * *